United States Patent [19]

Shalaby

[11] Patent Number: 5,522,842
[45] Date of Patent: Jun. 4, 1996

[54] ABSORBABLE E-CAPROLACTONE POLYMERS AS SUTURE COATINGS DISPLAYING AUTO CATALYZED HYDROLYSIS

[75] Inventor: Shalaby W. Shalaby, Guilford, Conn.

[73] Assignee: Poly-Med, Inc., Pendleton, S.C.

[21] Appl. No.: 212,174

[22] Filed: Mar. 11, 1994

[51] Int. Cl.$^6$ .............................. A61B 17/04; A61L 17/00
[52] U.S. Cl. ......................... 606/230; 525/354; 525/411; 525/415; 606/231
[58] Field of Search ................................. 606/228–231; 525/411, 415, 937, 354

[56] References Cited

U.S. PATENT DOCUMENTS

| | | | |
|---|---|---|---|
| 4,624,256 | 11/1986 | Messier et al. | 606/230 |
| 4,788,979 | 12/1988 | Jarrett et al. | 606/230 |
| 4,791,929 | 12/1988 | Jarrett et al. | 606/230 |
| 4,994,074 | 12/1991 | Bezwada et al. | 606/230 |
| 5,239,002 | 8/1993 | Ahmed et al. | 525/540 |

*Primary Examiner*—Gary Jackson

[57] ABSTRACT

Crystalline, low melting ε-Caprolactone polymers which undergo accelerated hydrolysis for use, for example, as absorbable coatings for surgical sutures; the polymers bearing basic amine functionalities, ionically or covalently linked to the ester chain, which induce autocatalyzed hydrolysis.

3 Claims, No Drawings

ABSORBABLE E-CAPROLACTONE POLYMERS AS SUTURE COATINGS DISPLAYING AUTO CATALYZED HYDROLYSIS

BACKGROUND OF THE INVENTION

This invention relates to crystalline, low melting ε-caprolactone polymers bearing basic amine functionalities which are linked to the ester chain ionically or covalently to induce catalyzed hydrolysis. The ester components can be derived from ε-caprolactone with or without small amounts of glycolide, and/or similar lactones. Such polymers with accelerated absorption profiles are especially adapted for use as transient coatings for absorbable multifilament surgical sutures.

Multifilament surgical sutures such as Dexon® polyglycolide multifilament suture typically require a surface coating to improve the handling and knotting characteristics of the suture. Capitalizing on the desirable low melting temperature, crystallinity, and rheological properties of polycaprolactone as a coating material, several compositions based on this polymer were investigated as coatings for surgical sutures. Recognizing the fact that the ε-caprolactone homopolymer is essentially non-absorbable led to the development of copolymers of ε-caprolactone with variable amounts of more absorbable monomers to improve the coating absorbability. U.S. Pat. No. 4,624,256 discloses a suture coating copolymer of at least 90 percent ε-caprolactone and a biodegradable monomer and optionally a lubricating agent. Examples of monomers for biodegradable polymers disclosed include glycolic acid and glycolide, as well as well-known monomers typically used to prepare absorbable polymer fibers or coatings for multifilament sutures. U.S. Pat. No. 4,788,979 and U.S. Pat. No. 4,791,929 disclose a bioabsorbable coating of a copolymer of at least 50 percent ε-caprolactone and glycolide. Sutures coated with such polymers are reported to be less stiff than sutures coated with other materials and the physical properties of the coated suture are also reported to be acceptable. U.S. Pat. No. 4,994,074 discloses copolymers of a predominant amount of ε-caprolactone, the balance being glycolide and glycolic acid; the use of glycolic acid reportedly increasing the rate of absorption of the copolymer when used as a coating for multifilament surgical sutures.

Unfortunately, the problem of adequate bioabsorbability of ε-caprolactone-based polymers without detrimental effects on their desirable properties as coatings still remains. Specifically, the use of sufficient amounts of glycolide to achieve sufficient absorbability of the copolymeric coating can compromise its crystallinity and melting characteristics, for it may become amorphous or liquid near room temperature. On the other hand, the strategy of using glycolic acid to achieve the reported results in coating absorbability does limit the ability to produce sufficiently long chain molecules to achieve optimum frictional properties, due to glycolic acid's known properties as both a ring-opening initiator and a chain terminator. Thus, a totally new approach to modifying the absorbability of polycaprolactone and its copolymers without affecting their desirable properties as suture coatings would be a more desirable goal.

SUMMARY OF THE INVENTION

One aspect of the invention are low melting, crystalline, basic nitrogenous polyesters, or polyesteramides, where the amine functionality represents between 1 and 10 percent of the total weight, while the repeat units of the polyester chain originate predominantly from ε-caprolactone. The balance ester sequences can be derived from glycolide, lactide p-dioxanone and/or one or more of the corresponding hydroxy acids. The amine functionality can be linked to the polyester chain ionically or covalently.

In another aspect, the invention is a coating for a surgical suture which displays autocatalyzed hydrolysis and improved absorbability over polyester coatings of the prior art which are devoid of any basic amine functionality. This coating comprises a low viscosity melt or a solution in an organic solvent, of the amine-bearing polyesters described above. Surprisingly, the incorporation of 1 to 5 percent of the amine functionality increased the polyester absorbability substantially, without compromising its desirable physical properties such as those associated with crystallinity and melting profile.

Polyesters bearing the amine-functionalities subject of this invention and coating derived therefrom can be used for coating bioabsorbable multifilament surgical sutures.

DETAILED DESCRIPTION OF THE INVENTION

Polyesters comprising predominantly ε-caprolactone polymer sequences generally refers to polymers with ε-caprolactone-based sequences of greater than 90 mole percent. ε-Caprolactone is the predominant component of the polyester because of its low melting, exceptionally low glass transition temperature (Tg) and its ability to enhance the physical properties of coated multifilament sutures. Preferably, the amount of ε-caprolactone used in the synthesis of the polyester ranges from 90 to 99, more preferably 96 to 99 mole percent. For copolyesters of this invention, the remaining comonomers are preferably glycolide and/or glycolic acid. Other lactones such as lactide and p-dioxanone and/or their corresponding hydroxy acids can be used. The hydroxy acids can be used, specifically, as chain initiators to control the polyester molecular weight, as determined in terms of their inherent viscosities (I.V.) as 0.1 g/dl solutions in hexafluoroisopropyl alcohol, and/or to provide chains with a carboxylic end group. The basic nitrogenous polyesters which are the subject of this invention, are to have I.V. of 0.05 to 0.35 dl/g and, preferably, 0.05 to 0.25 and, more preferably 0.10 to 0.20 dl/g.

Two major types of amine functionalities can be introduced into the polyester chain to accelerate its absorption through autocatalyzed hydrolysis. The weight percent of the amine functionalities in the polyesters subject of this invention can be between 1 and 5 and, preferably, 1 to 3. The first type of amine-functionality comprises an ionically linked mono- or poly-functional amine which is capable of forming a carboxylate salt with an acid-terminated polyester chain. This can entail, for instance, a caprolactone/glycolide copolymer made using catalytic amounts of stannous octoate and glycolic acid as the chain initiator, and following a typical reaction scheme established for caprolactone polymerization. The resulting acid terminated polyester is then allowed to form carboxylate salts with amine-bearing molecules: lysine, potassium lysinate or an alkane diamine, as depicted by structures A and B, respectively.

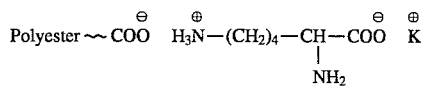

-continued (A)

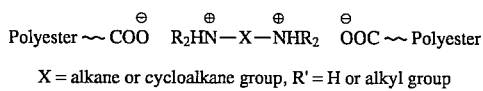

X = alkane or cycloalkane group, R' = H or alkyl group (B)

The second type of amine functionality is covalently incorporated into the polyester chain. This can be achieved by amidation of preformed polyester with di- or polyfunctional amine or using di- or poly-amine with at least one reactive hydrogen as the chain initiator, such as 1-methyl 4-aminomethyl-piperidine and 3,3'-diamino-N-methyldipropylamine. The ring opening polymerization can be achieved using catalytic amounts of stannous octoate. Typical polyesters covalently linked to the amine functionalities can be illustrated by structures C and D shown below.

n = 1 or 5

R = $CH_3$ or $C_2H_5$ —  (C)

X = alkane or cycloalkane group

n = 1 or 5

R = $CH_3$ or $C_2H_5$

X = Alkane or cycloalkane group  (D)

Although this invention addresses low melting crystalline polyesters made predominantly of ε-caprolactone, those skilled in the art can foresee the use of other aliphatic polyesters as the base materials and incorporate the amine functionality to the acid terminated polyester chains by salt formation or the amidation of pre-formed polyester chains using amino compounds similar to those associated with structures C and D above.

The coating can be applied to the braided suture as a low viscosity melt at temperatures between 70° and 100° C. and, preferably 70°–90° C. Excess coating can be removed by passing through a pad of non-woven fabric, e.g., polypropylene or a sizing die. More traditional methods of coating application can entail the use of 1 to 10 percent solution and, preferably, 2 to 5 percent in an organic solvent such as toluene at room temperature or between 25° and 50° C. The solvent can then be evaporated by air-drying at room temperature of between 25° and 75° C. Other solvents or mixture of solvents can be used as substitutes for toluene. The coated suture can be further treated thermally to insure even distribution of the coating on the braid components. Typical sutures which can be coated with compositions subject of this invention include those made of polyglycolide and polyethylene terephthalate. Depending on the suture size, the percent add-on of the coating can be varied between 1 and 10 percent and, preferably, 1.5 to 4.5 percent as the suture decreases from size #1 to size #50. At such level of coating, the suture handling and tie-down characteristics are improved substantially without compromising other properties such as visibility, surface appearance, and knot strength and security.

The absorption profile of the coating is such that it will not affect that of an absorbable suture to any discernable extent.

Typically, when representative coatings subject of this invention are used on polyethylene terephthalate sutures incubated in a phosphate buffer at 37° C. and pH of 7.26 lose 50–100 percent of their original mass in two to six months.

The following examples illustrate the claimed invention and are in no way intended to limit its scope.

EXAMPLE 1

Synthesis of acid-terminated polycaprolactone Polymer A

ε-Caprolactone (57.1 g, 0.5 mole) glycolic acid (7.6 g, 0.1 mole) and stannous octoate (0.5 ml of 0.1M solution in toluene, 20 mg, $5 \times 10^{-5}$ mole) were added to a glass reactor. The reactor was purged with dry nitrogen gas. The reactor was heated in an oil bath at 180° C., under nitrogen, for 12 hours while the contents were magnetically stirred. The resultant homopolymer has a Tg of −60° C. and Tm of 39° C. as measured by DSC. The resultant polymer inherent viscosity is 0.1 dl/g at 30° C. in hexafluoroisopropyl alcohol.

EXAMPLE 2

Preparation of potassium L-lysinate salt of Polymer A

Potassium L-lysinate (1.25 ml of 2.0M solution in methanol, 25 mmole), is slowly added with stirring to Polymer A (4.4 g, 25 mmole) in 100 ml tetrahydrofuran at room temperature. The tetrahydrofuran is then removed by vacuum. The structure of the resultant coating as an onium salt was determined by IR and NMR. The Tg and Tm were shown by DSC to be −62° and 44° C., respectively. Elemental analysis data were consistent with the proposed chemical structure:

|  | % N | % K |
| --- | --- | --- |
| Found | 1.52 | 2.23 |
| Calculated | 1.45 | 2.05 |

EXAMPLE 3

Synthesis of random copolymer of 98.5/1.5 caprolactone-glycolide, Copolymer B

ε-Caprolactone (57.1 g, 0.5 mole), glycolide (1.1 g, 9.5 mole), glycolic acid (7.6 g, 0.1 mole) and stannous octoate (0.5 ml of 0.1M solution in toluene, 20 mg, $5 \times 10^{-5}$ mole) were added to a glass reactor. The reactor was purged with dry nitrogen gas. The reactor was heated in an oil bath at 180° C. under nitrogen for 12 hours, while the contents were magnetically stirred. The final composition was determined by $^1$H NMR is shown to be essentially the same as the theoretical. The Tm is −62° C., and the Tg is 37° C.

EXAMPLE 4

Preparation of potassium L-lysinate salt of Copolymer B

Potassium L-lysinate (1.25 ml of 2.0M solution in methanol, 25 mmole), is slowly added with stirring to Polymer B (4.4 g, 2.5 mmole) in 100 ml tetrahydrofuran at room temperature. The tetrahydrofuran is then removed by vacuum. The structure of the resultant coating as an onium salt was determined by IR and NMR. The Tg and Tm were shown by DSC to be −60° and 39° C., respectively. Elemental analysis data were consistent with the proposed chemical structure:

|   | % N | % K |
|---|---|---|
| Found | 1.31 | 2.03 |
| Calculated | 1.45 | 2.05 |

EXAMPLE 5

Synthesis of random copolymer of 95/5 ε-caprolactone/ glycolide, Copolymer C

Following a procedure similar to that used for the synthesis of copolymer C B, copolymer was made and shown to have an inherent viscosity of 0.1 dl/g in HFIP at 25° C. It has a Tg of −60° C., and Tm of 40° C.

EXAMPLE 6

Preparation of potassium L-lysinate salt of Copolymer C

The salt is prepared following a procedure similar to that used for the preparation of the salt of Copolymer B. The composition of the resultant coating was consistent with its elemental analysis and NMR data. The Tg and Tm were shown by DSC to be −53° and 36° C., respectively.

EXAMPLE 7

Synthesis of acid-terminated polycaprolactone, Polymer D

ε-Caprolactone (57.1 g, 0.5 mole), lactic acid (9.0 g. 0.1 mole) and stannous octoate (0.5 ml of 0.1M solution in toluene, 20 mg, $5 \times 10^{-5}$ mole) were added to a glass reactor. The reactor was purged with dry nitrogen gas. The reactor was heated in an oil bath at 180° C., under nitrogen, for 12 hours, while the contents were magnetically stirred. The resulting Polymer D was removed and shown to have an inherent viscosity of 0.1 dl/g in hexafluoroisopropyl alcohol.

EXAMPLE 8

Preparation of amine-terminated polycaprolactone, Polymer E

ε-Caprolactone (57.1 g, 0.5 mole), 1-methyl-4-aminomethyl piperidine (2.54 g, 0.02 mole) and stannous octoate (0.5 ml. of 0.1M solution in toluene, 20 mg, $5 \times 10^{-5}$ mole) were transferred to a predried glass reactor under oxygen-free dry nitrogen atmosphere. The reaction mixture was heated to 170° C. under dry nitrogen. The polymerization was continued for 12 hours while the contents were magnetically stirred. The resulting Polymer E was removed and shown to have an inherent viscosity of 0.15 dl/g in hexafluoroisopropyl alcohol.

EXAMPLE 9

Preparation of polycaprolactone with internally placed amine functionality, Polymer F Using the same polymerization scheme as in Example 8 and all reagents except 1-methyl-4-aminomethyl piperidine, which was replaced by 3,3'-diamino-N-methyldipropylamine (2.32 g, 0.016 mole) to produce a polymer having an inherent viscosity of 0.13 dl/g.

EXAMPLE 10

Preparation of potassium L-lysinate salt of Polymer D

This is done following a procedure similar to that used for the preparation of the coating in Example 2.

EXAMPLE 11

Solution coating of size 2-0 polyglycolide braided suture

The suture is dipped 5–10 times in a 2 percent solution of the coating (from Examples 2, 4, or 6) in methylene chloride, with each coat dried in between dips. This yields a very thin homogeneous coating layer (typically 2.5 to 5 weight percent of the suture) which gives excellent knot tie-down properties both wet and dry, with no visible flaking.

EXAMPLE 12

Application of molten coating polymer to size 2-0 polyglycolide braided suture

The suture is passed through the molten coating (from Examples 2, 4, or 8) in a temperature of 5° to 50° C. above the melting temperature of the coating material, and then threaded through two non-woven Teflon® pads under slight compression to remove excess coating. This yields a thin, uniform coating layer (typically 5 weight percent of the suture). The coated suture exhibited excellent knot tie-down properties both wet and dry, with no visible flaking.

EXAMPLE 13

Absorption profiles of coatings

Depending on the composition of the polyester component, as in Examples 4 and 6, of the coating, and the level of amino groups, the mass loss ranges from 10 to 20 at three weeks, 40 to 50 at ten weeks, and 55 to 65 at thirteen weeks. To obtain accurate weight loss, a size 2-0 non-absorbable suture braid made of polyethylene terephthalate was used.

We claim:

1. A coated suture having a basic nitrogenous polyester polymer coating comprising 1 to 10 weight percent of the suture.

2. Absorbable multifilament sutures with a coating layer of crystalline nitrogenous polyester comprising predominantly ε-caprolactone polymer sequences linked ionically or covalently to amine-bearing structures which represent 1 to 10 percent of the total weight of the coating polymer.

3. Absorbable braided sutures with a coating layer of crystalline nitrogenous polyester comprising predominantly ε-caprolactone polymer sequences linked ionically or covalently to amine-bearing structures which represent 1 to 10 percent of the total weight of the coating polymer.

* * * * *